United States Patent

Hochido et al.

[11] Patent Number: 5,919,963
[45] Date of Patent: Jul. 6, 1999

[54] PROCESS FOR PURIFYING NIOBIUM ALKOXIDES AND TANTALUM ALKOXIDES

[75] Inventors: Yuukou Hochido, deceased, late of Saitama, by Youko Hochido, legal representative; Hidekimi Kadokura, Tokyo; Shuzo Tanabe; Riro Kobayashi, both of Saitama, all of Japan

[73] Assignee: Kabushikikaisha Kojundokagaku Kenkyusho, Saitama, Japan

[21] Appl. No.: 08/932,027

[22] Filed: Sep. 17, 1997

[30] Foreign Application Priority Data

Nov. 8, 1996 [JP] Japan ................................. 8-332628

[51] Int. Cl.⁶ .................................................... C07F 9/00
[52] U.S. Cl. .................................................. 556/42
[58] Field of Search ................................. 556/42

[56] References Cited

U.S. PATENT DOCUMENTS

| | | | |
|---|---|---|---|
| 4,525,468 | 6/1985 | Mack et al. | 502/104 |
| 4,830,879 | 5/1989 | Debsikdar | 427/162 |
| 5,508,063 | 4/1996 | Suzuki et al. | 427/255.3 |
| 5,616,410 | 4/1997 | Umezaki et al. | 428/323 |
| 5,679,815 | 10/1997 | Kirlin et al. | 556/42 |

*Primary Examiner*—Porfirio Nazario-Gonzalez
*Attorney, Agent, or Firm*—Fattibene & Fattibene; Paul A. Fattibene; Arthur T. Fattibene

[57] ABSTRACT

A process, excellent in the mass productivity and economization, for purifying a niobium alkoxide or tantalum alkoxide containing Fe, Ca, Sr, Na, U, etc. as impurities to attain a purity necessitated for electronic materials or the like is provided. A niobium alkoxide or tantalum alkoxide containing the above-described impurities is dissolved in a solvent to obtain a solution, 1 to 20% of the alkoxide in the solution is hydrolyzed under stirring to form a solid reaction product, and the reaction product is separated from the unreacted alkoxide by the distillation to recover the alkoxide.

1 Claim, No Drawings

PROCESS FOR PURIFYING NIOBIUM ALKOXIDES AND TANTALUM ALKOXIDES

FIELD OF THE INVENTION

The present invention relates to a process for purifying niobium alkoxides and tantalum alkoxides. In particular, the present invention relates to a process for removing a very small amount of impurity elements from niobium alkoxides and tantalum alkoxides.

BACKGROUND OF THE INVENTION

Niobium alkoxides and tantalum alkoxides are useful as starting materials for oxides including niobium oxides or tantalum oxides usable as materials for dielectrics. Such an alkoxide is calcined to form the powdery oxide; the alkoxide is hydrolyzed and then the hydrolyzate is calcined to form an oxide powder; the alkoxide is hydrolyzed, a coating film is formed from the hydrolyzate by the sol-gel method and then the film is burned to obtain an oxide film; or the alkoxide is used for forming an oxide film by MOCVD method. The composition of the oxides varies in a wide range from a single oxide to a composite oxides comprising plural components. When such an oxide is used as an electronic material for dielectrics, it is required to reduce the quantity of impurities such as transition metals typified by iron, alkali metals, e.g. sodium, alkaline earth metals, e.g. calcium, as well as uranium and thorium as far as possible. These impurity elements cause various disorders such as the reduction in the durability of electronic devices, increase in the leakage of current, and software errors. Recently, tantalum ethoxide is used for producing a tantalum oxide film which is a high dielectric constant paraelectric substance as a capacitor for DRAM (Dynamic Random Access Read/Write Memory) by MOCVD method. The use of niobium alkoxide or tantalum alkoxide as a starting material for a non-volatile memory by using a thin ferroelectric film of $SrBi_2Ta_2O_9$ or $SrBi_2Nb_2O_9$ will be further developed.

However, niobium alkoxides and tantalum alkoxides usually contain a very small amount of elements such as iron, calcium, sodium and uranium and compounds of them (hereinafter referred to as "impurities"). These impurities were incorporated thereinto from starting materials for the alkoxides or materials for the reactors; from the atmosphere surrounding the apparatuses, starting materials, intermediate materials and products; or from additives used for the synthesis or purification.

For removing the impurities from a niobium alkoxide or tantalum alkoxide, fractional distillation is considered to be easy. However, since the niobium alkoxide or tantalum alkoxide having a low vapor pressure necessitates the vacuum distillation, the separation and purification conducted taking the advantage of the difference in the vapor pressure between the alkoxide and the impurities is very difficult. Another disadvantage of this method is that the vapor pressure of the impurity is close to that of the niobium alkoxide or tantalum alkoxide, or that they form a double alkoxide to make the vapor pressures of them further closer. Still another disadvantage is that this method necessitates a complicated, expensive apparatus.

Japanese Patent Publication No. 58194/1989 discloses a process for purifying alkoxides of Al, Ga, In, Y, Si, Ti, Zr, etc. in the form of a solution and containing at least one of Ti, Fe, Cu, Si, Na and U impurities by hydrolyzing 0.1 to 50% of the metal alkoxides under stirring to form a solid reaction product and then separating the reaction product from the unreacted metal alkoxides by the distillation to recover the metal alkoxides. However, the specification is silent on niobium alkoxides and tantalum alkoxides which are pentavalent alkoxides. As for the degree of the purification, although the specification discloses that, for example, Fe content of aluminum isopropoxide as the starting material can be reduced from 750 ppm to 1 or <1 ppm by the purification, the specification is silent on the high degree of the purification intended by the inventors of the present invention which is about 0.01 to 0.001 ppm. In addition, the specification of Japanese Patent Publication No. 58194/1989 is silent on the removal of calcium and strontium.

The distillation is insufficient for the purification of niobium alkoxides and tantalum alkoxides having an ordinary purity to obtain a high purity. When impurities contained in niobium alkoxides and tantalum alkoxides in even only a very small amount of an order of ppb are not allowed, it is necessary to purify these alkoxides in the final stage of the production thereof because they are possibly contaminated in the course of the production of them even if the starting materials and additives are very carefully handled. However, efficient purification process which can be employed for this purpose on an industrial scale has not been developed yet.

The object of the present invention is to provide a process for efficiently removing a very small amount of impurities such as Fe, Ca, Sr, Na and U from niobium alkoxides and tantalum alkoxides to reduce the impurity level to an order of ppb.

SUMMARY OF THE INVENTION

After intensive investigations on the synthesis and purification of metal alkoxides and the analysis of minor impurities contained therein, the inventors have found that when a niobium alkoxide or tantalum alkoxide containing impurities is previously hydrolyzed under specified conditions and then distilled, the impurities are concentrated in the hydrolyzate and are substantially not contained in the distillate. The present invention has been completed on the basis of this finding. Namely, the present invention provides a process for purifying niobium alkoxides and tantalum alkoxides, characterized by dissolving a niobium alkoxide or tantalum alkoxide containing at least one of iron, calcium, stronitum sodium and uranium as impurities in a solvent to obtain a solution, hydrolyzing 1 to 20% of the alkoxide under stirring to form a solid reaction product, separating the reaction product from the unreacted alkoxide by distillation to recover the alkoxide.

DETAILED DESCRIPTION OF THE PREFERRED EMBODIMENTS

The metal alkoxides to be purified by the present invention are niobium alkoxides and tantalum alkoxides containing at least one of Fe, Ca, Sr, Na and U. The present invention is effective in removing also transition metal impurities such as Ni, Cr, Mn and Co contained in a very small amount. Although the impurity concentration is not particularly limited, usually a highly pure alkoxide having an impurity concentration of 1 to 0.001 ppm can be obtained from a starting alkoxide having an impurity concentration of 100 to 0.1 ppm.

The niobium alkoxides and tantalum alkoxides to be purified by the present invention are those which can be distilled. They include, for example, niobium pentamethoxide, niobium pentaethoxide, niobium pentapropoxide, niobium pentaisopropoxide, niobium pentabutoxide, niobium pentaisobutoxide, niobium pentatert-butoxide, niobium penta-sec-butoxide, tantalum pentamethoxide, tantalum pentaethoxide, tantalum pentapropoxide, tantalum pentaisopropoxide, tantalum pentabutoxide, tantalum pentaisobutoxide, tantalum penta-tert-butoxide and tantalum penta-sec-butoxide.

In the process of the present invention, a liquid alkoxide can be purified as it is or in the form of a solution thereof in an organic solvent; and a solid alkoxide can be purified after dissolving it in an organic solvent. The organic solvents include, for example, hydrocarbons such as hexane, heptane and cyclohexane; aromatic hydrocarbons such as benzene and toluene; ethers such as diethyl ether, tetrahydrofuran and dioxane; and alcohols having the same alkyl groups as those of the alkoxides.

In the process of the present invention, the alkoxide containing the impurities is kept in liquid form and about 1 to 20% thereof is hydrolyzed under stirring. The hydrolysis rate is herein defined to be the percentage of the quantity of water added in the purification treatment to the quantity of water necessitated for the following formal reaction formula:

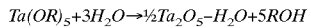

$$Ta(OR)_5 + 3H_2O \rightarrow \tfrac{1}{2}Ta_2O_5 - H_2O + 5ROH$$

(wherein R represents an alkyl group)

Namely, when 0.03 mol of water is added to 1 mol of $Ta(OR)_5$, the hydrolysis rate is 1%.

After the completion of the hydrolysis of a predetermined amount of the niobium alkoxide or tantalum alkoxide, the unreacted alkoxide becomes substantially free from the impurities and the impurities are contained in the solid or sol/gel reaction product supposedly because the hydrolysis of the impurities occurs simultaneously to the hydrolysis of the niobium alkoxide or tantalum alkoxide or the coprecipitation reaction of the impurities with niobium oxide hydrate or tantalum oxide hydrate occurs preferentially.

When the solution is hydrolyzed without the stirring, the reaction occurs only locally and, therefore, the impurities cannot be substantially removed.

Water used for the hydrolysis is not limited to the water but also include water vapor. Although it is preferred to feed water after diluting it by dissolving or dispersing in the organic solvent so as to prevent the localized reaction, the water can be fed also as it is.

The quantity of water used in the present invention is that corresponding to a hydrolysis rate of the niobium alkoxide or tantalum alkoxide of about 1 to 20%. When the hydrolysis rate is below 1%, the removal rate of the impurities is reduced and, on the contrary, a hydrolysis rate of above 20% is economically disadvantageous, though the impurity-removal rate is increased.

After the completion of the hydrolysis, the alkoxide hydrate is in the form of a sol/gel suspension. The solvent is directly distilled out and then the product is obtained by the distillation. As a matter of course, the products formed by the hydrolysis can be separated, if necessary, by leaving to stand, filtration, centrifugation or the like.

The distillation is an indispensable step in the present invention. When this step is omitted, the effective removal of the impurities is impossible. It is also a characteristic feature of the present invention that the distillation may be simple distillation without necessitating multi-stage rectification. Since niobium alkoxides and tantalum alkoxides are thermally stable and they can be distilled at a temperature of 200° C. or higher without thermal decomposition, even the compounds which are in solid form at room temperature can be distilled by elevating the temperature to the melting point thereof or above.

By the process of the present invention, the impurity concentration can be easily lowered, for example, from 100 ppm to 1 ppm or from 0.1 ppm to 0.001 ppm, to obtain the niobium alkoxides and tantalum alkoxides having an extremely high purity.

Thus, by the process of the present invention, recovered, unreacted alkoxides used in CVD method or alkoxides contaminated under unexpected conditions can be reused after the purification.

The following Examples will further illustrate the present invention.

EXAMPLE 1

51.3 g (125 mmol) of tantalum pentaethoxide and 32 ml of dehydrated ethanol were fed into a 100 ml flask having a stirrer, condenser, dropping funnel and thermometer. Water in an amount shown in Table 1 was diluted with 6 ml of dehydrated ethanol and added to the resultant mixture through a dropping funnel under stirring at 35° C. for a period of 20 minutes to hydrolyze tantalum pentaethoxide. After aging at 70° C. for 1 hour, the reaction liquid was in the form of a translucent sol. After distilling off ethanol under reduced pressure followed by simple distillation under 0.3 Torr, 39 g (96 mmol) to 41 g (101 mmol) of colorless, transparent tantalum pentaethoxide was obtained at a distillation temperature of 130° C. to 145° C. (yield: 76 to 80%). The concentrations of impurity elements in thus purified tantalum pentaethoxide are shown in Table 1.

It is apparent from the results that by hydrolyzing at least 1% of the starting alkoxide, the impurities can be effectively removed from the starting material. As shown in Comparative Example, the significant results cannot be obtained when the hydrolysis rate is 0.1%.

TABLE 1

| Sample No. | Starting material | Purified tantalum alkoxide | | |
|---|---|---|---|---|
| | | 1 | 2 | 3 (Comp. Ex.) |
| Amount of water added (g) | | 0.28 | 0.10 | 0.01 |
| Hydrolysis rate (%) | | 4.3 | 1.5 | 0.1 |
| Impurity conc. (ppm) | | | | |
| Fe | 0.20 | 0.002 | 0.010 | 0.13 |
| Ca | 0.37 | 0.001 | 0.005 | 0.21 |
| Sr | 0.05 | 0.001 | 0.001 | 0.03 |
| Na | 0.05 | <0.01 | <0.01 | 0.03 |
| U | 0.02 | <0.001 | <0.001 | 0.01 |

EXAMPLE 2

45.0 g (141 mmol) of niobium pentaethoxide and 35 ml of dehydrated toluene were fed into the same reactor as that used in Example 1. The resultant mixture was treated with 0.35 g (19 mmol) of water diluted with 7 ml of dehydrated ethanol under the same conditions as those in Example 1 (hydrolysis rate: 4.6 %). The solvent was distilled off under reduced pressure and then the simple distillation was conducted under 0.3 Torr to obtain 37 g (116 mmol) of colorless, transparent niobium pentaethoxide at a distillation temperature of 140° C. to 155° C. (yield: 82%). The concentrations of the impurity elements in the starting material and purified alkoxide are shown in Table 2.

TABLE 2

| Impurity conc. (ppm) | Starting material | Purified niobium alkoxide |
| --- | --- | --- |
| Fe | 0.60 | 0.005 |
| Ca | 0.25 | 0.001 |
| Sr | 0.05 | 0.001 |
| Na | 0.06 | <0.01 |
| U  | 0.02 | <0.001 |

According to the present invention, niobium alkoxides and tantalum alkoxides containing Fe, Ca, Sr, Na, U, etc. as impurities can be very easily purified.

What is claimed:

1. A process for purifying niobium alkoxides and tantalum alkoxides, characterized by dissolving a niobium alkoxide or tantalum alkoxide containing at least one of iron, calcium, strontium, sodium and uranium as impurities in a solvent to obtain a solution, hydrolyzing 1 to 20% of the alkoxide under stirring to form a solid reaction product, and separating the reaction product from the unreacted alkoxide by the distillation to recover the alkoxide.

* * * * *